US011072620B2

(12) United States Patent
Souza et al.

(10) Patent No.: US 11,072,620 B2
(45) Date of Patent: Jul. 27, 2021

(54) CRYSTALLINE FORMS OF PONATINIB HYDROCHLORIDE

(71) Applicant: Apotex Inc., Toronto (CA)

(72) Inventors: Fabio E. S. Souza, Mississauga (CA); Bahareh Khalili, Mississauga (CA); Katherine A. Rantanen, Burlington (CA); Jenny L. Gerster, Brantford (CA); Annyt Bhattacharyya, Hamilton (CA); Boris Gorin, Oakville (CA); Allan W. Rey, Brantford (CA)

(73) Assignee: Apotex Inc., Toronto (CA)

( * ) Notice: Subject to any disclaimer, the term of this patent is extended or adjusted under 35 U.S.C. 154(b) by 42 days.

(21) Appl. No.: 16/621,183

(22) PCT Filed: Jun. 15, 2018

(86) PCT No.: PCT/CA2018/050728
§ 371 (c)(1),
(2) Date: Dec. 10, 2019

(87) PCT Pub. No.: WO2018/232501
PCT Pub. Date: Dec. 27, 2018

(65) Prior Publication Data
US 2020/0095255 A1  Mar. 26, 2020

Related U.S. Application Data

(60) Provisional application No. 62/522,156, filed on Jun. 20, 2017.

(51) Int. Cl.
*C07D 487/04* (2006.01)
*A61P 35/02* (2006.01)
(52) U.S. Cl.
CPC ............ *C07D 487/04* (2013.01); *A61P 35/02* (2018.01); *C07B 2200/13* (2013.01)
(58) Field of Classification Search
CPC .... C07D 487/04; A61P 35/02; C07B 2200/13
See application file for complete search history.

(56) References Cited

U.S. PATENT DOCUMENTS

| 8,114,874 B2 | 2/2012 | Zou et al. |
| 9,493,470 B2 | 11/2016 | Murray et al. |
| 9,725,454 B2 | 8/2017 | Stefinovic et al. |

FOREIGN PATENT DOCUMENTS

| CA | 2916329 A1 | 1/2015 | |
| CN | 104650086 A | 5/2015 | |
| WO | 2007075869 A2 | 7/2007 | |
| WO | 2014093579 A2 | 6/2014 | |
| WO | WO 2014/093 579 A1 * | 6/2014 | ......... A61K 31/5025 |
| WO | 2015001098 A1 | 1/2015 | |
| WO | 2015085971 A1 | 6/2015 | |
| WO | 2015085972 A1 | 6/2015 | |
| WO | 2015085973 A1 | 6/2015 | |

OTHER PUBLICATIONS

Bernstein, Polymorphism in Molecular Crystals, 2002, pp. 9-10, Oxford University Press, New York, US.
Huang et al., "Discovery of 3-[2-(Imadazo[1,2-b]pyridazin-3yl)ethynyl]-4-methyl-N-{4-[(4-methylpiperazin-1-yl)-methyl]-3-(trifluoromethyl)phenyl}benzamide (AP24534), a Potent, Orally Active Pan-Inhibitor of Breakpoint Cluster Region-Abelson (BCR-ABL) Kinase Including the T315l Gatekeeper Mutant", Journal of Medicinal Chemistry, 2010, pp. 4701-4719, vol. 53, No. 12.
Porter, "Coating of Pharmaceutical Dosage Forms", Remington the Science and Practice of Pharmacy, 2006, pp. 929-938, 21st Edition, Lippincott Williams & Wilkins, Philadelphia, US.
Rudnic et al., "Oral Solid Dosage Forms", Remington the Science and Practice of Pharmacy, 2006, pp. 889-928, 21st Edition, Lippincott Williams & Wilkins, Philadelphia, US.
"Impurities: Guideline for Residual Solvents Q3C(R5)", International Conference on Harmonisation of Technical Requirements for Registration of Pharmaceuticals for Human Use, 2011, 29 pages, Step 4 Version.

* cited by examiner

*Primary Examiner* — Erich A Leeser
(74) *Attorney, Agent, or Firm* — The Webb Law Firm

(57) ABSTRACT

The present invention provides novel crystalline forms of Ponatinib hydrochloride. Specific crystalline forms provided by the present invention include Ponatinib hydrochloride Form APO-I, APO-III and APO-IV, each of which is obtained from acetonitrile/formic acid solutions. Additionally, Form APO-V is provided, which is obtained from concentrated hydrochloric acid.

16 Claims, 4 Drawing Sheets

CRYSTALLINE FORMS OF PONATINIB HYDROCHLORIDE

CROSS-REFERENCE TO RELATED APPLICATIONS

This application is the United States national phase of International Application No. PCT/CA2018/050728 filed Jun. 15, 2018, and claims priority to U.S. Provisional Patent Application No. 62/522,156 filed Jun. 20, 2017 the disclosures of which are hereby incorporated by reference in their entirety.

TECHNICAL FIELD

The present invention is directed to novel crystalline forms of Ponatinib hydrochloride and processes for the preparation thereof.

BACKGROUND

The compound 3-(imidazo[1,2-b]pyridazin-3ylethynyl)-4-methyl-N-{4-[(4-methylpiperazin-1-yl)methyl]-3-(trifluoromethyl)phenyl}benzamide hydrochloride commonly known as Ponatinib hydrochloride, is described in WO 2007/075869 A2 as a monohydrochloride (shown in structure (1)) and J. Med. Chem. 2010, 53, 4701-4719 as a trihydrochloride. Ponatinib hydrochloride, a kinase inhibitor, is marketed in the United States as ICLUSIG®, and is indicated for the treatment of certain types of leukemia.

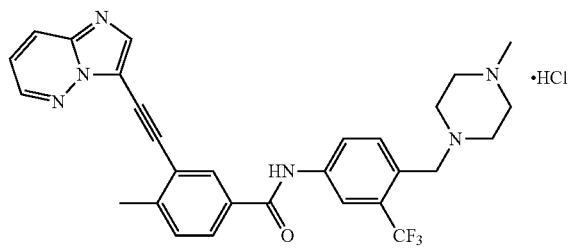

(1)

Crystalline forms of Ponatinib hydrochloride, including anhydrous and solvated forms are reported, for example, in WO 2014/093579 A2, WO 2015/001098 A1, WO 2015/085973 A1 and CN104650086 A. However, these reported crystalline forms of Ponatinib hydrochloride are associated with various problems, such as poor aqueous solubility, hygroscopicity, poor crystallinity, poor crystalline homogeneity (i.e., mixtures of crystalline forms), the incorporation or use of toxic or questionable solvents for which no adequate safety data is available according to established ICH (International Council for Harmonisation of Technical Requirements for Pharmaceuticals for Human Use) guidelines such as Q3C(R5), preparations that are not reproducible, or that are impractical for commercial use.

Different crystalline forms of the same compound may have different packing, thermodynamic, spectroscopic, kinetic, surface and mechanical properties. For example, different crystalline forms may have different stability properties. A particular crystalline form may be more sensitive to heat, relative humidity (RH) and/or light. Alternatively or additionally, a particular crystalline form may provide more compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more resistant to flow, or may be more difficult to filter and/or wash.

Although general approaches to crystalline form screening of active pharmaceutical ingredients are known, it is well established that the prediction of whether any given compound will exhibit polymorphism is not possible. Furthermore, prediction of the properties of any unknown crystalline forms, and how they will differ from other crystalline forms of the same compound, remains even more elusive (Joel Bernstein, Polymorphism in Molecular Crystals, Oxford University Press, New York, 2002, page 9).

Therefore, there exists a need for novel crystalline forms of Ponatinib hydrochloride for use in providing improved drug products containing Ponatinib hydrochloride and their manufacture.

SUMMARY

The Ponatinib hydrochloride crystalline forms of the present invention exhibit differences in properties when compared to the known crystalline forms of Ponatinib hydrochloride. Properties that differ between the invention and known crystalline forms of Ponatinib hydrochloride include the following: packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, compactibility, tableting, handling, flow, and blending. Additionally, the crystalline forms of the present invention meet the criteria established by ICH guidelines, such as Q3C(R5), outlining acceptable levels of residual solvents in pharmaceutical substances. While some embodiments of the present invention contain formic acid, which is an allowable Class 3 solvent (a solvent with low toxic potential), the present invention surprisingly controls the level of acetonitrile, a Class 2 solvent (solvents that should be limited owing to toxic effects), such that negligible amounts of acetonitrile are present in the crystalline forms of the invention.

Differences in the properties of the crystalline forms of the present invention provide practical advantages that can be exploited to meet specific needs in the manufacture and formulation of Ponatinib hydrochloride. For example, the forms of the present invention are amenable to scale up for efficient industrial production using standard batch-type manufacturing equipment. Furthermore, the crystalline forms of the present invention exhibit stability during preparation, handling and storage.

Accordingly, in a first aspect of the present invention, there is provided a crystalline form of Ponatinib hydrochloride, APO-I, characterized by a powder X-ray diffraction (PXRD) diffractogram comprising peaks, expressed in degrees 2θ (±0.2°), at 8.8°, 9.6° and 13.2°. In a preferred embodiment of the first aspect, the PXRD diffractogram further comprises peaks, expressed in degrees 2θ (+0.2°), at 14.4° and 23.0°. In a further preferred embodiment of the first aspect, the PXRD diffractogram further comprises peaks, expressed in degrees 2θ (+0.2°), at 14.4°, 16.5°, 18.7°, 19.2° and 23.0°. In another preferred embodiment of the first aspect, Form APO-I comprises formic acid in a weight percent of at least approximately 3.9 wt %, more preferably, within the range of at least approximately 3.9 wt % and 7.5 wt %. In an additional preferred embodiment of the first aspect, Form APO-I comprises Ponatinib hydrochloride and formic acid in a molar ratio of between approximately 1:0.5 and approximately 1:1. In a further preferred embodiment of the first aspect, the crystalline Form APO-I provides a PXRD diffractogram comprising peaks in substantially the same positions (approximately ±0.2° 2θ) as those shown in FIG. 1.

In a second aspect of the present invention, there is provided a crystalline form of Ponatinib hydrochloride, APO-III, characterized by a PXRD diffractogram comprising peaks, expressed in degrees 2θ (±0.2°), at 9.0°, 10.1° and 12.0°. In a preferred embodiment of the second aspect, the PXRD diffractogram further comprises peaks, expressed in degrees 2θ (±0.2°), at 13.6°, 14.2° and 27.0°. In another preferred embodiment of the second aspect, Form APO-III comprises formic acid in a weight percent of less than approximately 7.5 wt %, and more preferably, between approximately 0.5 wt % and 7.5 wt %. In an additional preferred embodiment of the second aspect, Form APO-III further comprises, in addition to formic acid, water in a weight percentage of between approximately 3.5 wt % and approximately 5.2 wt %. In a further preferred embodiment of the second aspect, the crystalline Form APO-III provides a PXRD diffractogram comprising peaks in substantially the same positions (approximately ±0.2° 2θ) as those shown in FIG. 2.

In a third aspect of the present invention, there is provided a crystalline form of Ponatinib hydrochloride, APO-IV, characterized by a PXRD diffractogram comprising peaks, expressed in degrees 2θ (±0.2°), at 7.7°, 9.2°, 11.2° and 17.5°. In a preferred embodiment of the third aspect, the PXRD diffractogram further comprises at least two peaks, expressed in degrees 2θ (±0.2°), selected from the group consisting of 13.5°, 14.4°, 14.9°, 16.5°, 17.5° and 22.9°. In a further preferred embodiment of the third aspect, the PXRD diffractogram further comprises peaks, expressed in degrees 2θ (±0.2°), at 13.5°, 14.4°, 14.9°, 16.5°, 17.5° and 22.9°. In another preferred embodiment of the third aspect, Form APO-IV comprises formic acid in a weight percent of less than approximately 2.0 wt %, and more preferably, between approximately 0.1 wt % and 1.0 wt %. In preferred embodiments of the third aspect, Form APO-IV comprises a water content between approximately 2.7 wt % and 4.1 wt %. In a further preferred embodiment of the third aspect, the crystalline Form APO-IV provides a PXRD diffractogram comprising peaks in substantially the same positions (approximately ±0.2° 2θ) as those shown in FIG. 3.

In a fourth aspect of the present invention, there is provided a crystalline form of Ponatinib hydrochloride, APO-V, characterized by a PXRD diffractogram comprising peaks, expressed in degrees 2θ (±0.2°), at 7.2°, 9.6° and 11.5°. In a preferred embodiment of the fourth aspect, the PXRD diffractogram further comprises peaks, expressed in degrees 2θ (±0.2°), at 5.8°, 8.8° and 15.2°. In a further preferred embodiment of the fourth aspect, the crystalline Form APO-V provides a PXRD diffractogram comprising peaks in substantially the same positions (approximately ±0.2° 2θ) as those shown in FIG. 4.

In a fifth aspect of the present invention, there is provided a pharmaceutical composition comprising a crystalline form of Ponatinib hydrochloride according to any one of the first, second, third or fourth aspects of the invention, and one or more pharmaceutically acceptable excipients. Preferably, the pharmaceutical composition is in the form of a solid dosage form. Most preferably, the pharmaceutical composition is a tablet.

In a sixth aspect of the present invention, there is provided a use of a crystalline form of Ponatinib hydrochloride according to any one of the first, second, third or fourth aspects of the invention, or the pharmaceutical composition of the fifth aspect of the invention, in the treatment of leukemia.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example, with reference to the attached Figures.

DETAILED DESCRIPTION

Figure 1:
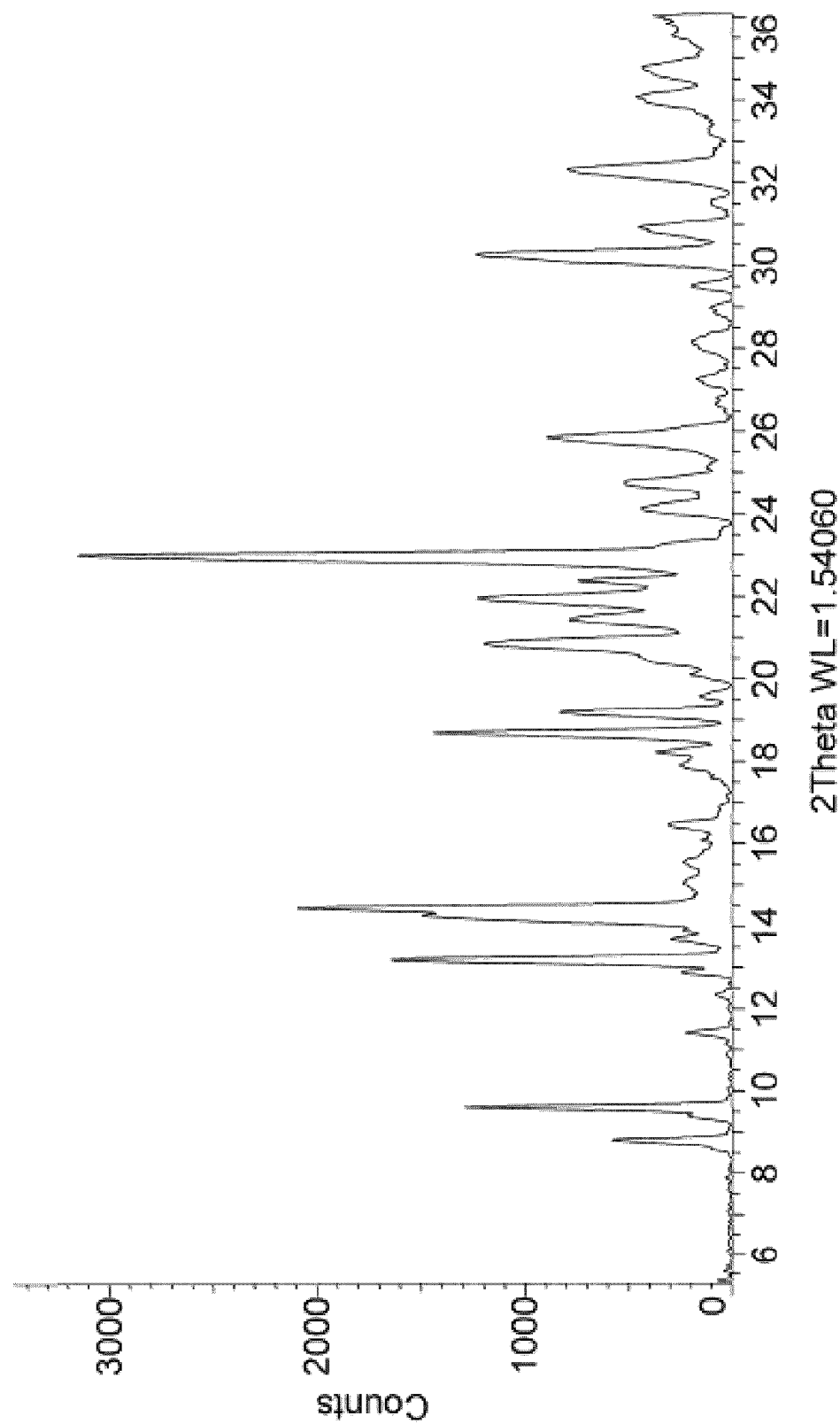
FIG. 1 is a representative PXRD diffractogram of Ponatinib Hydrochloride Form APO-I as prepared in Example 1.

The present invention provides novel crystalline forms of Ponatinib hydrochloride exhibiting beneficial differences in properties when compared to the known crystalline forms of Ponatinib hydrochloride, thereby addressing problems associated with known crystalline forms of Ponatinib hydrochloride. Properties that differ between the crystalline forms of the present invention and known crystalline forms of Ponatinib hydrochloride include, depending on the particular embodiment of the invention, packing properties such as molar volume, density and hygroscopicity; thermodynamic properties such as melting and solubility; kinetic properties such as dissolution rate and chemical/polymorphic stability; surface properties such as crystal habit; and/or mechanical properties such as hardness, tensile strength, compactibility, tableting, handling, flow, and blending. These differences in properties may be exploited to provide practical advantages over the known forms of Ponatinib hydrochloride to aid in meeting specific needs in the manufacture and formulation of Ponatinib hydrochloride. Additionally, the crystalline forms of the present invention meet the criteria established by ICH guidelines, such as Q3C(R5), outlining acceptable levels of residual solvents in pharmaceutical substances. While some embodiments of the present invention contain formic acid, which is an allowable Class 3 solvent (a solvent with low toxic potential), the present invention surprisingly controls the level of acetonitrile, a Class 2 solvent (solvents that should be limited owing to toxic effects), to permissible levels. This allows the crystalline forms of the present invention to be prepared by processes that are amenable to application on an industrial scale.

Depending on the manner in which the embodiments of the invention are prepared, the methodology and instrument used for PXRD analysis, the intensity of a given peak observed in the PXRD diffractogram may vary when compared to the same peak in the representative PXRD diffractograms provided in FIGS. 1 to 4. Thus, differences in relative peak intensities between peaks in a PXRD diffractogram for a given crystalline form may be observed when compared to the relative peak intensities of the peaks in the representative PXRD diffractograms of FIGS. 1 to 4. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIGS. 1 to 4, it is understood that individual peak positions may vary between ±0.2° 2θ from the values observed in the representative PXRD diffractograms provided in FIGS. 1 to 4 for the crystalline forms of the invention, or listed in Tables 1 to 4. Such variations are known and understood by a person of skill in the art, and any such variations do not depart from the invention disclosed herein.

Further, it is understood that, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1 to 4. Thus, PXRD diffractograms of the crystalline forms of the present invention may, in some circumstances, display the same relative peak positions as observed in the representative PXRD diffractograms provided in FIGS. 1 to 4, with the exception that each peak is offset in the same direction, and by approximately the same amount, such that the overall PXRD diffractogram is substantially the same in appearance as a PXRD diffractogram of FIGS. 1 to 4, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 1 to 4 for the crystalline forms of the invention.

As used herein, the term 'crystalline form' refers to a substance with a particular arrangement of molecular components in its crystal lattice, and which may be identified by physical characterization methods such as PXRD. The multi-component crystalline forms of the present invention, which comprise Ponatinib hydrochloride and other molecules, such as formic acid and water in Forms APO-I, APO-III and APO-IV, may exhibit variability in the exact molar ratios of their components depending on the conditions used in their preparation. Thus, where reference is made to relative amounts of Ponatinib hydrochloride and other molecules, such as formic acid and water, within a specific crystalline form, these amounts should be seen as being relative amounts. In practice, the molar ratio of the components may vary by ±20% from a stated amount. For example, with respect to the present invention, a molar ratio of 1:0.5 should be understood to include the ratios 1:0.4 and 1:0.6, as well as all of the individual ratios in between.

As used herein, when referring to solvent content, the term "weight percentage" (wt %) refers to the ratio: weight solvent/(weight solvent+weight Ponatinib hydrochloride), expressed as a percentage.

As used herein, the term "room temperature" refers to a temperature in the range of 20° C. to 25° C.

Unless defined otherwise herein, the term "approximately", when used in reference to a weight percentage, allows for a variance of plus or minus 10%.

As used herein, the term "volumes" refers to the parts of solvent or liquids by volume (mL) with respect to the weight of solute (g). For example, when an experiment is conducted using 1 g of starting material and 100 mL of solvent, it is said that 100 volumes of solvent are used.

When practising the embodiments of the present invention as described herein, variances to a given temperature or time that would be understood or expected by the person skilled in the art to provide substantially the same result may be employed. For example, when reference is made to a particular temperature, it is to be understood that there is an allowable variance of ±5° C. associated with that temperature. When reference is made to a particular time, it is to be understood that there is an allowable variance of ±10 minutes when the time is one or two hours, and ±1 hour when longer periods of time are indicated.

In a first embodiment of the present invention, there is provided a new crystalline form of Ponatinib hydrochloride, Ponatinib hydrochloride Form APO-I.

Ponatinib hydrochloride Form APO-I can be characterized by a PXRD diffractogram comprising, among other peaks, characteristic peaks, expressed in degrees 2θ (±0.2°), at 8.8°, 9.6° and 13.2°. Preferably, the PXRD diffractogram further comprises peaks, expressed in degrees 2θ (±0.2°), at 14.4° and 23.0°. More preferably, the PXRD diffractogram further comprises peaks, expressed in degrees 2θ (±0.2°), at 14.4°, 16.5°, 18.7°, 19.2° and 23.0°. PXRD studies of capped and uncapped samples of Ponatinib Form APO-I have shown that this form is polymorphically stable following storage in a stability chamber maintained at 40° C./75% RH for at least 6 days.

An illustrative PXRD diffractogram of Ponatinib hydrochloride Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the Ponatinib hydrochloride Form APO-I of the present invention, the relative intensities of the peaks are variable. Thus, depending on a particular sample, the prominence or relative intensity of individual peaks may differ from those in the representative PXRD diffractogram and peak listing for Form APO-I provided in FIG. 1 and Table 1.

TABLE 1

Relative peak intensities of Ponatinib Hydrochloride Form APO-I from FIG. 1

| Angle (°2θ) | Relative intensity (%) |
| --- | --- |
| 8.80 | 18.3 |
| 9.60 | 40.9 |
| 11.40 | 7.0 |
| 13.18 | 52.0 |
| 14.43 | 66.4 |
| 16.47 | 9.5 |
| 18.68 | 45.6 |
| 19.19 | 26.3 |

TABLE 1-continued

Relative peak intensities of Ponatinib Hydrochloride Form APO-I from FIG. 1

| Angle (°2θ) | Relative intensity (%) |
| --- | --- |
| 20.84 | 38.0 |
| 21.43 | 24.8 |
| 21.94 | 39.1 |
| 22.37 | 23.5 |
| 22.97 | 100.0 |
| 24.13 | 13.9 |
| 24.74 | 16.5 |
| 25.84 | 28.3 |

TABLE 2

Figure 2:
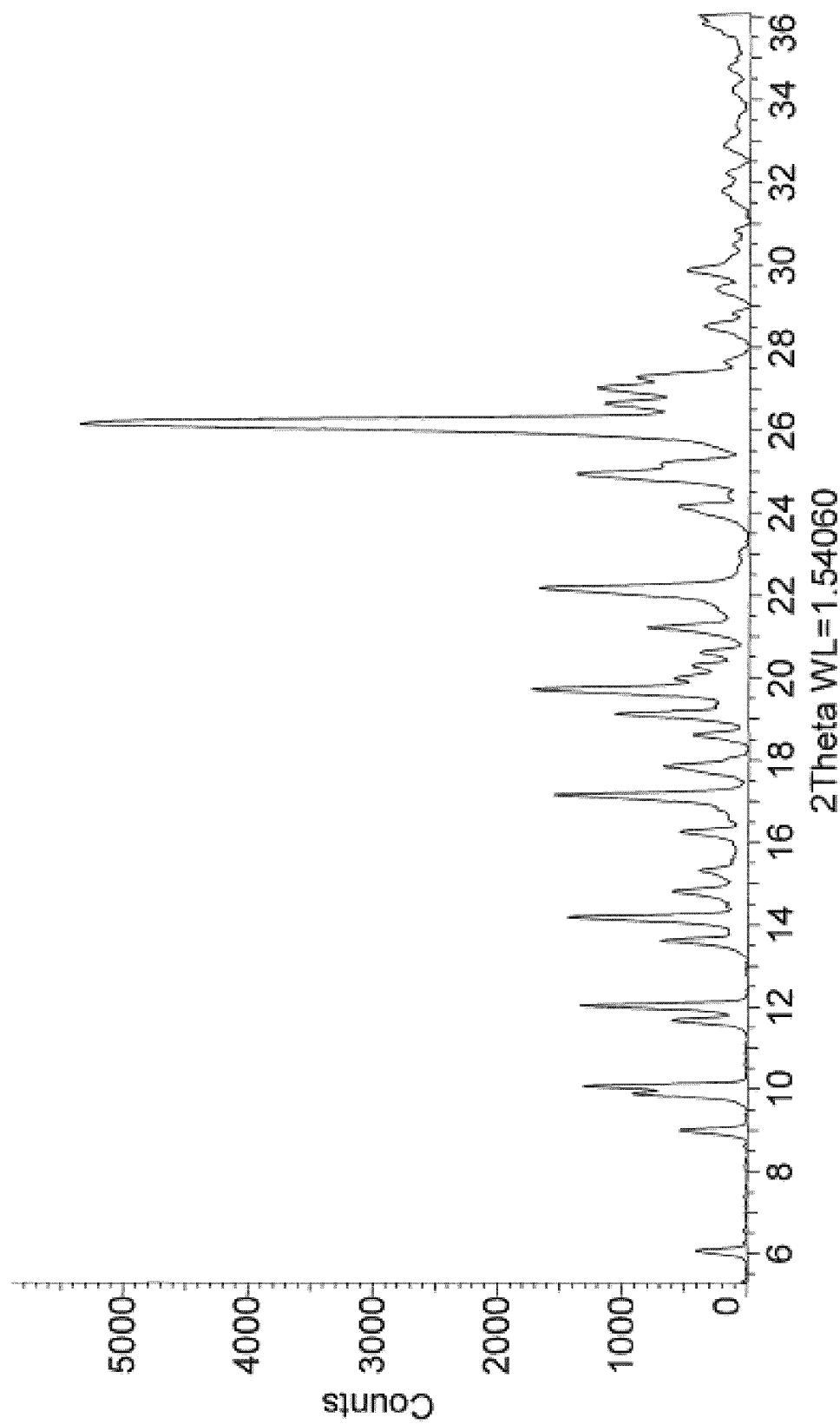
FIG. 2 is a representative PXRD diffractogram of Ponatinib Hydrochloride Form APO-III as prepared in Example 2.

Relative peak intensities of Ponatinib Hydrochloride Form APO-III from FIG. 2

| Angle (°2θ) | Relative intensity (%) |
| --- | --- |
| 6.05 | 6.4 |
| 8.96 | 9.0 |
| 10.06 | 21.1 |
| 11.66 | 10.9 |
| 12.02 | 24.2 |
| 13.60 | 12.9 |
| 14.16 | 25.8 |
| 14.80 | 11.3 |
| 15.32 | 6.8 |
| 16.23 | 9.3 |
| 22.15 | 29.9 |
| 24.92 | 23.9 |
| 26.98 | 20.1 |

As described in Example 1, Ponatinib hydrochloride Form APO-I can be prepared by heating a suspension of Ponatinib hydrochloride in acetonitrile to approximately 50° C., adding formic acid until dissolution or near dissolution is achieved, conducting a clarifying filtration, and rapidly cooling the mixture to room temperature or below, during which time crystallization occurs. Filtration and drying of the resulting material provides Ponatinib hydrochloride Form APO-I. Preferably, in the preparation of Form APO-I, the formic acid is provided as an anhydrous reagent having a water content of equal to or less than approximately 1 wt %.

Ponatinib hydrochloride Form APO-I can be further characterized based on the amount of formic acid present within the crystalline form. In general, Form APO-I is typically isolated having a weight percentage of formic acid of at least approximately 3.9 wt %, and preferably a weight percentage of formic acid of between approximately 3.9 wt % and approximately 7.5 wt %. Preferably, the molar ratio of Ponatinib hydrochloride to formic acid in Form APO-I is in the range of approximately 1.0:0.5 and approximately 1:1.

In a second embodiment of the present invention, there is provided a new crystalline form of Ponatinib hydrochloride, Ponatinib hydrochloride Form APO-III.

Ponatinib hydrochloride Form APO-III can be characterized by a PXRD diffractogram comprising, among other peaks, characteristic peaks, expressed in degrees 2θ (±0.2°), at 9.0°, 10.1° and 12.0°. Preferably, the PXRD diffractogram further comprises peaks, expressed in degrees 2θ (±0.2°), at 13.6°, 14.2° and 27.0°. PXRD studies of capped samples of Ponatinib Form APO-III have shown that this form is polymorphically stable following storage in a stability chamber maintained at 27° C./60% RH for at least 7 days.

An illustrative PXRD diffractogram of Ponatinib hydrochloride Form APO-III, as prepared in Example 2, is shown in FIG. 2. A peak listing, comprising representative peaks from the PXRD diffractogram in FIG. 2, and their relative intensities, is provided in Table 2. Although illustrative of the PXRD diffractogram that is provided for the Ponatinib hydrochloride Form APO-III of the present invention, the relative intensities of the peaks are variable. Thus, depending on a particular sample, the prominence or relative intensity of individual peaks may differ from those in the representative PXRD diffractogram and peak listing for Form APO-III provided in FIG. 2 and Table 2.

As described in Examples 2-5, Ponatinib hydrochloride Form APO-III can be prepared by providing a mixture of Ponatinib hydrochloride, acetonitrile and minimal quantities of formic acid. Preferably, an amount of formic acid of between approximately 0.5 volumes to approximately 1 volume of formic acid with respect to Ponatinib hydrochloride is used. Preferably, the mixture also contains traces of water, more preferably approximately 0.5 mole equivalents to approximately 1.5 mole equivalents of water with respect to Ponatinib hydrochloride. This water can be provided through the use of commercially available, non-anhydrous formic acid, or through the addition of water to the mixture. Preferably, the mixture is heated at an elevated temperature, for example, approximately 50° C., for a period, prior to cooling to room temperature or below. Filtration and drying of the resulting material provides Ponatinib hydrochloride Form APO-III.

Ponatinib hydrochloride Form APO-III can be further characterized based on the amount of formic acid and water present within the crystalline form. In general, Form APO-III is typically isolated having a weight percentage of formic acid of at less than approximately 7.5 wt %, and preferably a weight percentage of formic acid of between approximately 0.5 wt % and approximately 7.5 wt %. Additionally, Form APO-III is typically isolated having a weight percentage of water of between approximately 3.5 wt % and approximately 5.2 wt %.

In a third embodiment of the present invention, there is provided a new crystalline form of Ponatinib hydrochloride, Ponatinib hydrochloride Form APO-IV.

Ponatinib hydrochloride Form APO-IV can be characterized by a PXRD diffractogram comprising, among other peaks, characteristic peaks, expressed in degrees 2θ (±0.2°), at 7.7°, 9.2°, 11.2° and 17.5°. Preferably, the PXRD diffractogram further comprises at least two peaks, expressed in degrees 2θ (±0.2°), selected from the group consisting of 13.5°, 14.4°, 14.9°, 16.5°, 17.5° and 22.9°. More preferably, the PXRD diffractogram further comprises peaks, expressed in degrees 2θ (±0.2°), at 13.5°, 14.4°, 14.9°, 16.5°, 17.5° and 22.9°. Studies have shown that when stored under conditions of ambient temperature and humidity, Ponatinib Form APO-IV is polymorphically and chemically stable as measured by PXRD and HPLC, respectively, for at least 4 months. Furthermore, a PXRD study showed that Ponatinib Form APO-IV is polymorphically stable following storage at room temperature and 90% RH for at least 24 hours.

Figure 3:
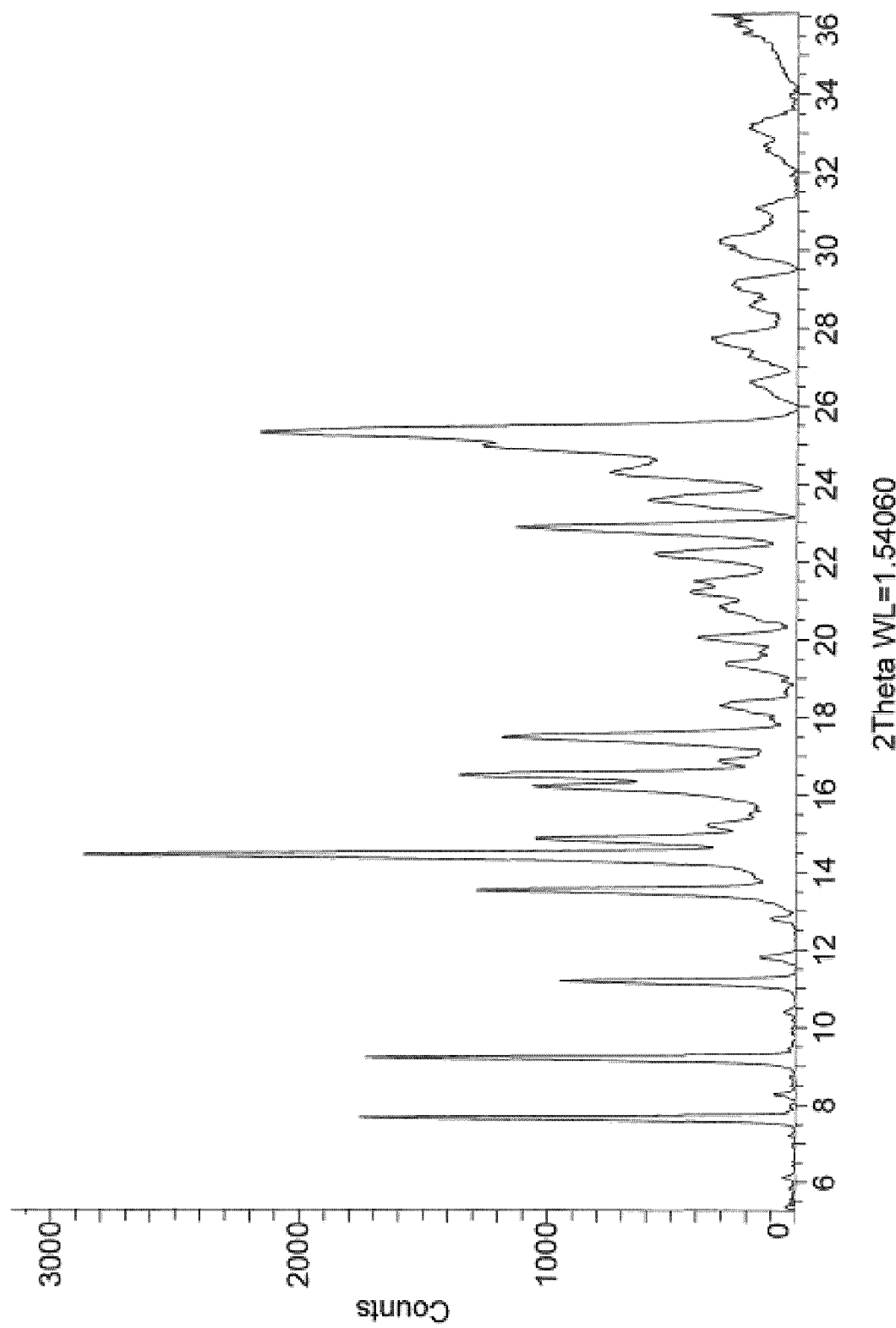
FIG. 3 is a representative PXRD diffractogram of Ponatinib Hydrochloride Form APO-IV as prepared in Example 6.

An illustrative PXRD diffractogram of Ponatinib hydrochloride Form APO-IV, as prepared in Example 6, is shown in FIG. 3. A peak listing, comprising representative peaks from the PXRD diffractogram in FIG. 3, and their relative intensities, is provided in Table 3. Although illustrative of the PXRD diffractogram that is provided for the Ponatinib hydrochloride Form APO-IV of the present invention, the relative intensities of the peaks are variable. Thus, depending on a particular sample, the prominence or relative intensity of individual peaks may differ from those in the representative PXRD diffractogram and peak listing for Form APO-IV provided in FIG. 3 and Table 3.

TABLE 3

Relative peak intensities of Ponatinib Hydrochloride Form APO-IV from FIG. 3

| Angle (°2θ) | Relative intensity (%) |
|---|---|
| 7.66 | 60.8 |
| 9.20 | 60.5 |
| 11.18 | 32.9 |
| 13.53 | 44.7 |
| 14.43 | 100.0 |
| 14.85 | 36.6 |
| 16.19 | 36.8 |
| 16.50 | 47.3 |
| 17.47 | 41.3 |
| 18.30 | 10.7 |
| 19.37 | 10.0 |
| 20.05 | 13.9 |
| 22.21 | 20.0 |
| 22.86 | 39.3 |
| 23.58 | 20.9 |
| 24.28 | 26.4 |
| 25.29 | 75.5 |

As described in Examples 6 and 7, Ponatinib hydrochloride Form APO-IV can be prepared by providing a mixture of Ponatinib hydrochloride, acetonitrile, minimal quantities of both formic acid and water. Preferably, the amounts of each of formic acid and water are in the range of 0.5 to 1 volume with respect to Ponatinib hydrochloride. Preferably, the mixture is heated at an elevated temperature, for example, approximately 50° C., for a period, prior to cooling to room temperature or below. Filtration and drying of the resulting material provides Ponatinib hydrochloride Form APO-IV.

Ponatinib hydrochloride Form APO-IV can be further characterized based on the amount of formic acid present within the crystalline form. In general, Form APO-IV is typically isolated having a weight percentage of formic acid of less than approximately 2.0 wt %, and preferably a weight percentage of formic acid of between approximately 0.1 wt % and approximately 1.0 wt %.

In a fourth embodiment of the present invention, there is provided a new crystalline form of Ponatinib hydrochloride, Ponatinib hydrochloride Form APO-V.

Ponatinib hydrochloride Form APO-V can be characterized by a PXRD diffractogram comprising, among other peaks, characteristic peaks, expressed in degrees 2θ (±0.2°), at 7.2°, 9.6° and 11.5°. Preferably, the PXRD diffractogram further comprises peaks, expressed in degrees 2θ (±0.2°), at 5.8°, 8.8° and 15.2°.

Figure 4:
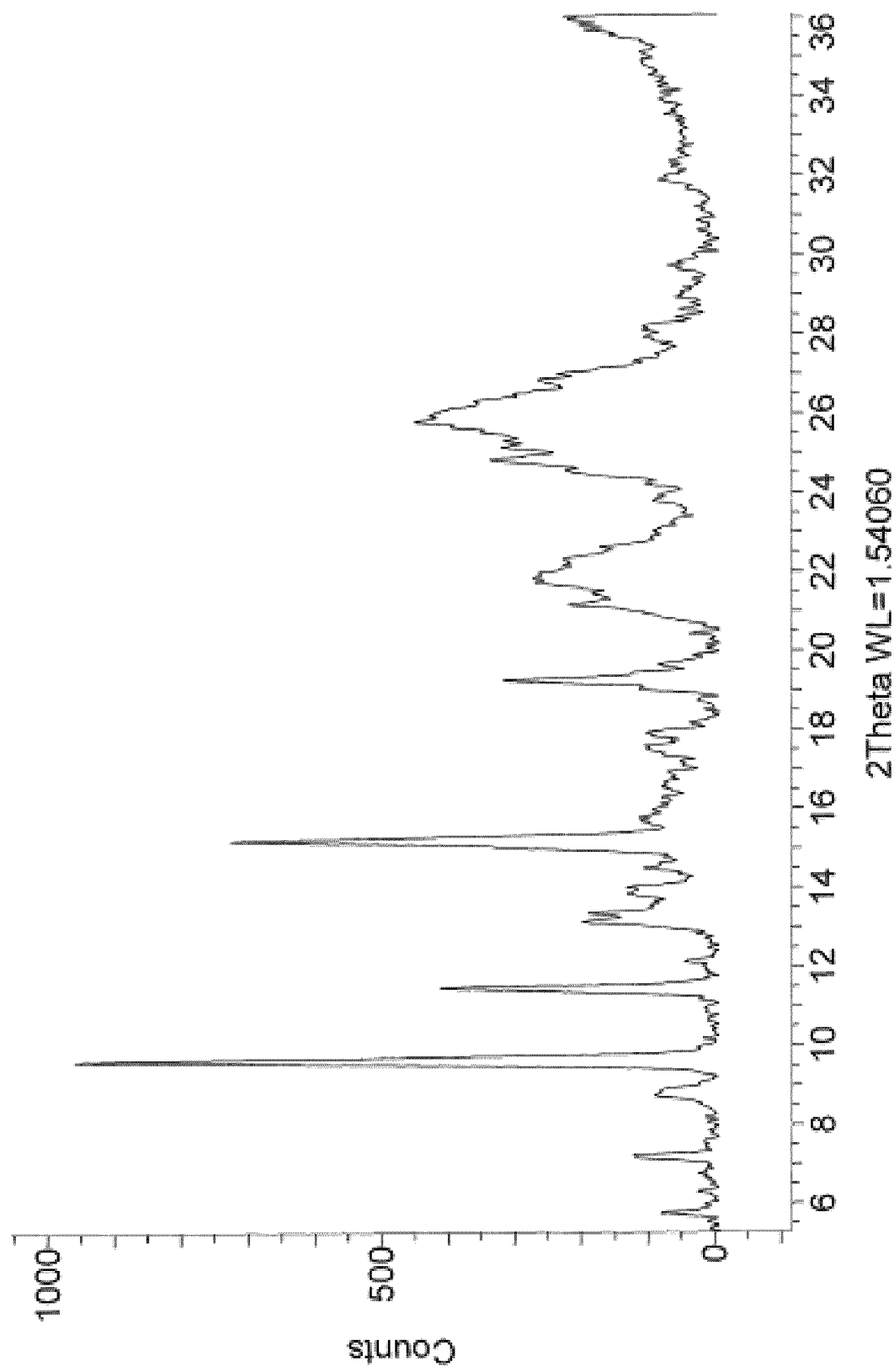
FIG. 4 is a representative PXRD diffractogram of Ponatinib Hydrochloride Form APO-V as prepared in Example 8.

An illustrative PXRD diffractogram of Ponatinib hydrochloride Form APO-V, as prepared in Example 8, is shown in FIG. 4. A peak listing, comprising representative peaks from the PXRD diffractogram in FIG. 4, and their relative intensities, is provided in Table 4. Although illustrative of the PXRD diffractogram that is provided for the Ponatinib hydrochloride Form APO-V of the present invention, the relative intensities of the peaks are variable. Thus, depending on a particular sample, the prominence or relative intensity of individual peaks may differ from those in the representative PXRD diffractogram and peak listing for Form APO-V provided in FIG. 4 and Table 4.

TABLE 4

Relative peak intensities of Ponatinib Hydrochloride Form APO-V from FIG. 4

| Angle (°2θ) | Relative intensity (%) |
|---|---|
| 5.77 | 8.3 |
| 7.21 | 12.6 |
| 8.81 | 8.5 |
| 9.61 | 100.0 |
| 11.45 | 43.1 |
| 13.15 | 20.5 |
| 15.18 | 75.9 |
| 19.25 | 33.1 |

As described in Example 8, Ponatinib hydrochloride Form APO-V can be prepared by treating a solution of Ponatinib hydrochloride in excess concentrated aqueous hydrochloric acid with acetone. Preferably, the process is conducted at room temperature. Filtration and drying of the resulting material provides Ponatinib hydrochloride Form APO-V.

In a further embodiment of the invention, there is provided a pharmaceutical composition of Ponatinib hydrochloride Form APO-I, Ponatinib hydrochloride Form APO-III, Ponatinib hydrochloride Form APO-IV or Ponatinib hydrochloride Form APO-V, with one or more pharmaceutically acceptable excipients. Preferably, the pharmaceutical composition is a solid dosage form suitable for oral administration, such as a capsule, tablet, pill, powder or granulate. Most preferably, the pharmaceutical composition is a tablet. Preferably, the pharmaceutical composition provides a dose of Ponatinib hydrochloride that is equivalent to the 15 mg, 30 mg or 45 mg of Ponatinib hydrochloride found in ICLUSIG® drug products.

Suitable pharmaceutically acceptable excipients are preferably inert with respect to the crystalline forms of Ponatinib hydrochloride of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrollidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required. Suitable excipients and the preparation of solid oral dosage forms are well known to person of skill in the art, and are described generally, for example, in *Remington The Science and Practice of Pharmacy* 21$^{st}$ Edition (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in *Remington The Science and Practice of Pharmacy* 21$^{st}$ Edition (Lippincott Williams & Wilkins: Philadelphia; 2006; Chapter 46).

EXAMPLES

The following non-limiting examples are illustrative of some of the aspects and embodiments of the invention described herein.

The Ponatinib hydrochloride used as a starting material in the following examples was consistent with Form A Ponatinib hydrochloride, which is reported in WO 2014/093579 A2. Other polymorphic forms are equally suitable as starting material when preparing the novel crystalline forms of Ponatinib hydrochloride of the present invention. The water content of the formic acid used in the following examples was between about 0.9 wt % and 1.9 wt % by Karl Fischer (KF) analysis.

PXRD Analysis:

PXRD diffractograms were recorded on a Bruker D8 DISCOVER powder X-ray diffractometer (Bruker-AXS, Karlsruhe, Germany). The sample holder was oscillated along X and Y axes during the measurement. The generator was a Micro-focus X-ray source (IMSTube: Cu tube, 1.54184 Å) with a voltage of 50 kV and current of 1.00 mA, using a divergence slit of 0.3 mm and collimator of 0.3 mm. For each sample, one frame was collected (2theta: 20.00°, Omega: 5.00°) using a still scan with a Pilatus 3R-100 kA detector over 300 seconds at the distance of 154.72 mm from the sample. Raw data were evaluated using the program EVA (Bruker-AXS, Karlsruhe, Germany).

Example 1: Preparation of Ponatinib Hydrochloride Form APO-I

Ponatinib hydrochloride (50 mg, 0.088 mmol) was weighed into a small vial, suspended in acetonitrile (0.5 mL), and heated to 50° C. in a reactor block. Formic acid (35 μL) was slowly added dropwise over 10 minutes until near complete dissolution, giving a slightly turbid solution. The mixture was clarified by hot filtration through a 0.45 μM filter into a vial and allowed to cool rapidly in ambient conditions before application of ice cooling. After 1 hour of ice cooling, no precipitation was observed and the vial was placed under refrigeration conditions for 4 days during which time crystallization occurred. The solid was collected by filtration to afford Ponatinib hydrochloride Form APO-I as a white crystalline material. $^1$H-NMR (acetic acid-d$_4$) of the sample showed approximately 6.4 wt % formic acid. $^1$H-NMR (DMSO-d$_6$) of the sample failed to identify the presence of any meaningful amount of acetonitrile in the material. The PXRD diffractogram of a sample prepared by this method is shown in FIG. 1.

Example 2: Preparation of Ponatinib Hydrochloride Form APO-III

Ponatinib hydrochloride (50 mg, 0.088 mmol) was weighed into a small vial, suspended in acetonitrile (0.5 mL), and placed inside a reactor block pre-heated to 50° C. Upon equilibrating the suspension for 45 minutes, three portions of formic acid (10 μL/portion) were added at 10 minutes intervals and the mixture was maintained for 30 minutes further at 50° C. An additional quantity of formic acid was added (5 μL) and the suspension became a slightly turbid yellow solution. Upon further stirring for 1 hour at 50° C., the solution was clarified by hot filtration (through a 0.45 μm filter) into a vial heated to 50° C. At the elevated temperature, a precipitate was observed to form rapidly (within 5 minutes), and controlled cooling was applied over 30 minutes to adjust the temperature of the suspension to 37° C. Heating was discontinued and the suspension stirred overnight at room temperature and then maintained at 0-5° C. for approximately 2 hours. The solid was collected by filtration to afford Ponatinib hydrochloride Form APO-III as a white crystalline material. $^1$H-NMR (DMSO-d$_6$) of the sample showed approximately 3.1 wt % formic acid. The PXRD diffractogram of a sample prepared by this method is shown in FIG. 2.

Example 3: Preparation of Ponatinib Hydrochloride Form APO-III

Ponatinib hydrochloride (50 mg, 0.088 mmol) was weighed into a small vial, suspended in a mixture of acetonitrile (0.5 mL, 10 vol) and formic acid (35 μL). The vial was placed inside a reactor block pre-heated to 50° C. Upon stirring for 1.5 hours, the mixture remained a suspension. The mixture was then heated at 60° C. for 30 minutes, and subsequently treated with two additional quantities of formic acid (0.5 μL each) followed by stirring for 30 minutes and 1 hour, respectively. The suspension was cooled to room temperature and a sample was removed for PXRD analysis. The result obtained was consistent with the formation of Form APO-III. To the remainder of the suspension was added water (10 μL) and the mixture stirred at 50° C. for 18 hours. Essentially complete dissolution was observed, and to maximize the solubilization, the solution was stirred at slightly elevated temperature (60-70° C.) for 30 minutes. The solution was clarified by hot filtration and allowed to stir at 50° C. for 30 minutes before cooling to room temperature outside the reactor block. The resulting solid was isolated by filtration, washed with acetonitrile and dried under vacuum aspiration to afford Ponatinib hydrochloride Form APO-III. The PXRD diffractogram of this material was consistent with that shown in FIG. 2. Upon drying the material at room temperature in vacuo for about 21.5 hours, $^1$H-NMR (acetic acid-d$_4$) analysis showed approximately 2.3 wt % formic acid.

Example 4: Preparation of Ponatinib Hydrochloride Form APO-III

Ponatinib hydrochloride (300 mg, 0.53 mmol) was weighed into a small vial and suspended in acetonitrile (3 mL). Formic acid (300 μL), containing 1-2% water, was added and the vial placed inside a pre-heated oil bath set at 60° C. and maintained for 3 hours. The temperature was then reduced to 40° C. and the mixture maintained for an additional 3 hours. Heating was discontinued and the mixture was stirred at ambient temperature overnight. The resulting solid was isolated by filtration and dried in vacuo at room temperature for 4 hours to afford Ponatinib hydrochloride Form APO-III as a white crystalline material (106 mg). The PXRD diffractogram of this material was consistent with that shown in FIG. 2. $^1$H-NMR (acetic acid-$d_4$) analysis showed approximately 7.5 wt % formic acid. The water content (KF) of the sample was 4.3 wt %.

Example 5: Preparation of Ponatinib Hydrochloride Form APO-III

A suspension of Ponatinib hydrochloride (500 mg, 0.88 mmol) in acetonitrile (5 mL) and formic acid (350 µL) was placed in an oil bath pre-heated to 50° C. and stirred for 3 hours. The slurry was removed from the heat and cooled to room temperature. A small sample of solid was isolated, with PXRD analysis showing consistency with the formation of Form APO-III. After 1 hour, the remainder of the solid was isolated by filtration, washed with cold acetonitrile (2 mL) and dried in vacuo at room temperature for 45 minutes to afford Ponatinib hydrochloride Form APO-III as a white crystalline material (185 mg, 37% yield). The PXRD diffractogram of this material was consistent with that shown in FIG. 2. $^1$H-NMR (acetic acid-$d_4$) analysis showed approximately 7.5 wt % formic acid. TGA analysis (25-300° C.@10° C./min; 85 mL/min $N_2$ flow) of the sample showed a first weight loss of 4.3% between 39° C. and 138° C. and a second weight loss of 5.7% between 138° C. and 207° C.

Example 6: Preparation of Ponatinib Hydrochloride Form APO-IV

A suspension of Ponatinib hydrochloride (500 mg, 0.88 mmol) in acetonitrile (5 mL) and formic acid (350 µL) was placed in an oil bath pre-heated to 50° C. and stirred for 45 minutes. Water (500 µL) was added to the suspension, which led to rapid dissolution of the solid material. Upon stirring for 45 minutes at 50° C., the solution was clarified by hot filtration through a 0.45 µm filter and, upon stirring a further 30 minutes, heating was discontinued, and the flask allowed to reach room temperature by slow cooling in the oil bath. Substantial precipitation was observed after 3.5 hours, and the mixture was stirred at room temperature overnight (17 hours). The resulting solid was isolated by filtration, washed with cold acetonitrile (2 mL) and dried in vacuo for 1 hour at room temperature to afford Ponatinib hydrochloride Form APO-IV (248 mg, 50% yield). The PXRD diffractogram of a sample prepared by this method is shown in FIG. 3. $^1$H-NMR (acetic acid-$d^4$) of the sample showed approximately 0.6 wt % formic acid. TGA analysis (25-300° C.@10° C./min; 85 mL/min $N_2$ flow) of the sample showed a first weight loss of 3.4% between 39.5° C. and 168° C., and a second weight loss of 0.9% between 168° C. and 199° C.

Example 7: Preparation of Ponatinib Hydrochloride Form APO-IV

Ponatinib hydrochloride (50 mg, 0.088 mmol) was weighed into a small vial, suspended in acetonitrile (0.5 mL, 10 vol) and placed inside a reactor block pre-heated to 50° C. Formic acid (total volume: 35 µL) was then added portion-wise over 45 minutes (3 portions of 10 µL each and one portion of 5 µL) and the resulting suspension was stirred for an additional 75 minutes. Upon treatment with water (50 µL), rapid dissolution of the solid material was observed. After stirring for 10 minutes, the solution was clarified by hot filtration and the temperature of the resulting solution was reduced to 45° C. Precipitation was noted after 2 hours, at which time a sample was removed for PXRD analysis. The result obtained from PXRD analysis was consistent with the formation of Form APO-IV. The remaining mixture was allowed to stir at room temperature for 19 hours, after which the solid was isolated by filtration. The PXRD diffractogram of this material was consistent with that shown in FIG. 3 for Form APO-IV. Upon drying the material for 45 minutes at room temperature in vacuo, $^1$H-NMR (acetic acid-$d_4$) analysis showed approximately 0.6 wt % formic acid.

Example 8: Preparation of Ponatinib Hydrochloride Form APO-V

Acetone (1.4 mL, 13 vol) was added dropwise over 10 minutes at room temperature to a solution of Ponatinib hydrochloride (107 mg, 0.19 mmol) in concentrated hydrochloric acid (0.3 mL), causing immediate precipitation of a solid. The suspension was diluted with acetone (0.8 mL) prior to isolation of the solid by filtration. Brief drying under aspiration following by drying in vacuo for 10 minutes afforded Ponatinib hydrochloride Form APO-V. The PXRD of a sample prepared by this method is shown in FIG. 4.

What is claimed is:

1. A crystalline form of Ponatinib hydrochloride, characterized by a powder X-ray diffraction (PXRD) diffractogram comprising peaks, expressed in degrees 2θ (±) 0.2°, at 7.7°, 9.2°, 11.2° and 17.5°.

2. The crystalline form of claim 1, characterized by a PXRD diffractogram further comprising at least two peaks, expressed in degrees 2θ (±0.2°), selected from the group consisting of 13.5°, 14.4°, 14.9°, 16.5°, 17.5° and 22.9°.

3. The crystalline form of claim 1, characterized by a PXRD diffractogram further comprising peaks, expressed in degrees 2θ (±0.2°), at 13.5°, 14.4°, 14.9°, 16.5°, 17.5° and 22.9°.

4. The crystalline form of claim 2, having a weight percentage of water of between approximately 2.7 wt % and 4.1 wt %.

5. The crystalline form of claim 1, providing a PXRD diffractogram comprising peaks in substantially the same positions (approximately ±0.2° 2θ) as those shown in FIG. 3.

6. A crystalline form of Ponatinib hydrochloride, characterized by a powder X-ray diffraction (PXRD) diffractogram comprising peaks, expressed in degrees 2θ (±0.2°), at 8.8°, 9.6° and 13.2°.

7. The crystalline form of claim 6, characterized by a PXRD diffractogram further comprising peaks, expressed in degrees 2θ (±0.2°), at 14.4° and 23.0°.

8. The crystalline form of claim 6, characterized by a PXRD diffractogram further comprising peaks, expressed in degrees 2θ (±0.2°), at 14.4°, 16.5°, 18.7°, 19.2° and 23.0°.

9. The crystalline form of claim 6, having a weight percentage of formic acid of at least approximately 3.9 wt %.

10. The crystalline form of claim 6, having a weight percentage of formic acid of between approximately 3.9 wt % and approximately 7.5 wt %.

11. The crystalline form of claim 6, having a molar ratio of Ponatinib hydrochloride to formic acid of between approximately 1:0.5 and approximately 1:1.

12. The crystalline form of claim 6, providing a PXRD diffractogram comprising peaks in substantially the same positions (approximately ±0.2° 2θ) as those shown in FIG. 1.

13. A pharmaceutical composition comprising the crystalline form of Ponatinib hydrochloride of claim 1, and one or more pharmaceutically acceptable excipients.

14. The crystalline form of claim 3, having a weight percentage of water of between approximately 2.7 wt % and 4.1 wt %.

15. The crystalline form of claim 2, providing a PXRD diffractogram comprising peaks in substantially the same positions (approximately ±0.2° 2θ) as those shown in FIG. 3.

16. The crystalline form of claim 3, providing a PXRD diffractogram comprising peaks in substantially the same positions (approximately ±0.2° 2θ) as those shown in FIG. 3.

\* \* \* \* \*

UNITED STATES PATENT AND TRADEMARK OFFICE
CERTIFICATE OF CORRECTION

PATENT NO. : 11,072,620 B2
APPLICATION NO. : 16/621183
DATED : July 27, 2021
INVENTOR(S) : Fabio E. S. Souza et al.

It is certified that error appears in the above-identified patent and that said Letters Patent is hereby corrected as shown below:

In the Claims

Column 14, Line 32, Claim 1, delete "($\pm$) 0.2°," and insert -- ($\pm$0.2°), --

Signed and Sealed this
Twenty-sixth Day of April, 2022

Katherine Kelly Vidal
*Director of the United States Patent and Trademark Office*